United States Patent [19]

Cruz

[11] 4,449,984
[45] May 22, 1984

[54] CONTAINER HAVING AN AIR TIGHT SEAL
[75] Inventor: Exequiel D. Cruz, Palatine, Ill.
[73] Assignee: Respiratory Care, Inc., Arlington Heights, Ill.
[21] Appl. No.: 391,914
[22] Filed: Jun. 24, 1982
[51] Int. Cl.³ .................. A61F 5/44; B65D 25/14
[52] U.S. Cl. ........................ 604/319; 220/293; 220/298; 220/404; 220/410; 604/317
[58] Field of Search ............. 220/404, 410, 293, 298; 604/35, 317, 319, 220, 323, 324, 326

[56] References Cited
U.S. PATENT DOCUMENTS

| | | |
|---|---|---|
| 2,126,159 | 8/1938 | Wilcox . |
| 2,885,107 | 5/1959 | Bliss .................. 220/410 X |
| 2,920,788 | 1/1960 | Emerson . |
| 3,052,371 | 9/1962 | Van Bemmelen ............ 220/404 X |
| 3,070,275 | 12/1962 | Bostrom .................... 220/404 X |
| 3,127,049 | 3/1964 | Welty et al. . |
| 3,550,803 | 12/1970 | Pelli ........................ 220/404 X |
| 3,719,197 | 3/1973 | Pannier, Jr. et al. . |
| 3,805,018 | 4/1974 | Luong et al. ................. 220/410 |
| 3,863,634 | 2/1975 | Reynolds et al. ............ 604/320 X |
| 3,955,572 | 5/1976 | Martin . |
| 4,027,777 | 6/1977 | Blanke ................. 215/DIG. 1 X |
| 4,033,345 | 7/1977 | Sorenson et al. . |
| 4,085,751 | 4/1978 | Dodge . |
| 4,111,204 | 9/1978 | Hessel . |
| 4,122,973 | 10/1978 | Ahern . |
| 4,151,929 | 5/1979 | Sapien ...................... 220/404 |
| 4,245,637 | 1/1981 | Nichols ..................... 604/320 |
| 4,321,922 | 3/1982 | Deaton .................... 220/404 X |

OTHER PUBLICATIONS

"The CRD System for Suction Collection, Retention, and Disposal", Inservice Training Manual and Instructions for Use, by Medi-Van Corp., Box 2816, Abilene, Texas 79604, 1980, (Distributed by American Hospital Supply, 1450 Waukegan Road, McGaw Park, IL, USA 60085).

Primary Examiner—Allan N. Shoap
Attorney, Agent, or Firm—Eric P. Schellin

[57] ABSTRACT

A container, and more specifically a medical suction container, that comprises a canister, a lid and a liner that together form an air tight seal. Opposed wedge-shaped camming blocks mounted on the lid and the canister force the lid and liner into a sealing mating relationship thereby forming the seal. The canister and liner have similar sealing assemblies that consist of upwardly extending portions that form aligned notches. The lid with a sealing protrusion is mated with a notch of the liner, which in turn forces the liner into the notch of the canister. A locking lip on the liner engages a lip on the sealing protrusion thereby locking the lid to the liner.

9 Claims, 11 Drawing Figures

CONTAINER HAVING AN AIR TIGHT SEAL

BACKGROUND OF THE INVENTION

1. Field of the Invention

The present invention relates to an air tight container, and more specifically to a medical suction container. The principal feature of the present invention is the air tight seal between the container lid and the canister liner.

2. Description of the Prior Art

To maintain a vacuum within a container it is necessary to provide an air tight seal between the covering lid and the material holding canister. In some applications, it may also be desirable to insert a disposable liner within the canister and as such an air tight seal may have to be provided between the liner and the lid.

The main application of the present invention is in medical suction containers in which fluid from a patient is sucked into the container vacuum and therein stored. It is desirable, because of the disease-bearing nature of the removed fluids to have a disposable liner for such containers. Heretofore, liners have been welded or adhesively secured to the inside cover of a medical suction container as illustrated by Reynolds et al. U.S. Pat. No. 3,863,634. After the medical suction procedure has been completed the cover with liner is discarded.

In addition, liners have been disposed between the canister body and the lid of an industrial drum. As disclosed by Zilbert U.S. Pat. No. 4,094,432, a liner having a screw threaded annular portion is secured between a drum and its top.

The present invention provides an air tight seal between the lid and the canister liner so that a vacuum can be maintained within the canister liner. In particular, a sealing assembly on the liner cooperates with a sealing protrusion on the lid to form an air tight seal.

SUMMARY OF THE INVENTION

According to the invention there is provided a container having a lid and a canister. Within the canister is inserted a canister lining that has a sealing assembly that mates with a sealing protrusion on the lid to form an air tight seal between the lid and the liner. Opposed engaging camming surfaces on the lid and the canister force the sealing protrusion of the lid into a mating position with the sealing assembly of the liner.

The sealing assembly of the liner comprises two upwardly extending protruding portions between which is formed a liner notch. In addition, on one of the protruding portions is a locking lip. The sealing protrusion of the lid is forced into a mating position with the liner notch and is locked in place by the locking lip which engages a lip on the sealing protrusion.

The opposed engaging camming surfaces of the lid and the canister comprise wedge-shaped blocks. The camming surfaces of the blocks engage when the lid is rotated with respect to the canister and thereby force the sealing protrusion into a mating position with the liner notch.

The canister has a similar sealing assembly with respect to the liner sealing assembly. The canister sealing assembly forms a canister notch which is aligned with the liner notch. Opposed cooperating aligning surfaces on the canister sealing assembly and the liner sealing assembly serve to position the liner notch over the canister notch.

When sealing the canister, the lid is rotated forcing the sealing protrusion into a mating position with the liner notch. The sealing protrusion mates with the liner notch and forces the base portion of the liner notch into the canister notch. The locking lip of the liner sealing assembly locks the sealing protrusion into mating position by engaging the lip of the sealing protrusion.

The medical suction container may have a canister with a flat bottom or a canister with a concave bottom with legs to provide lateral stability on flat horizontal surfaces. The lid of the container has a suction egress conduit port, a patient ingress conduit port and a spout. In addition, in some embodiments an additional vent conduit port is provided in the lid which communicates by a flexible hose with a vent in the bottom of the canister.

DETAILED DESCRIPTION OF THE PREFERRED EMBODIMENTS

The following description of the present invention is illustrative of a medical suction container, but the present invention may be used on any container where an air tight seal must be maintained between a canister lining and a lid. Therefore the following description is not intended to be a limiting example of the uses of the present invention.

Figure 2:
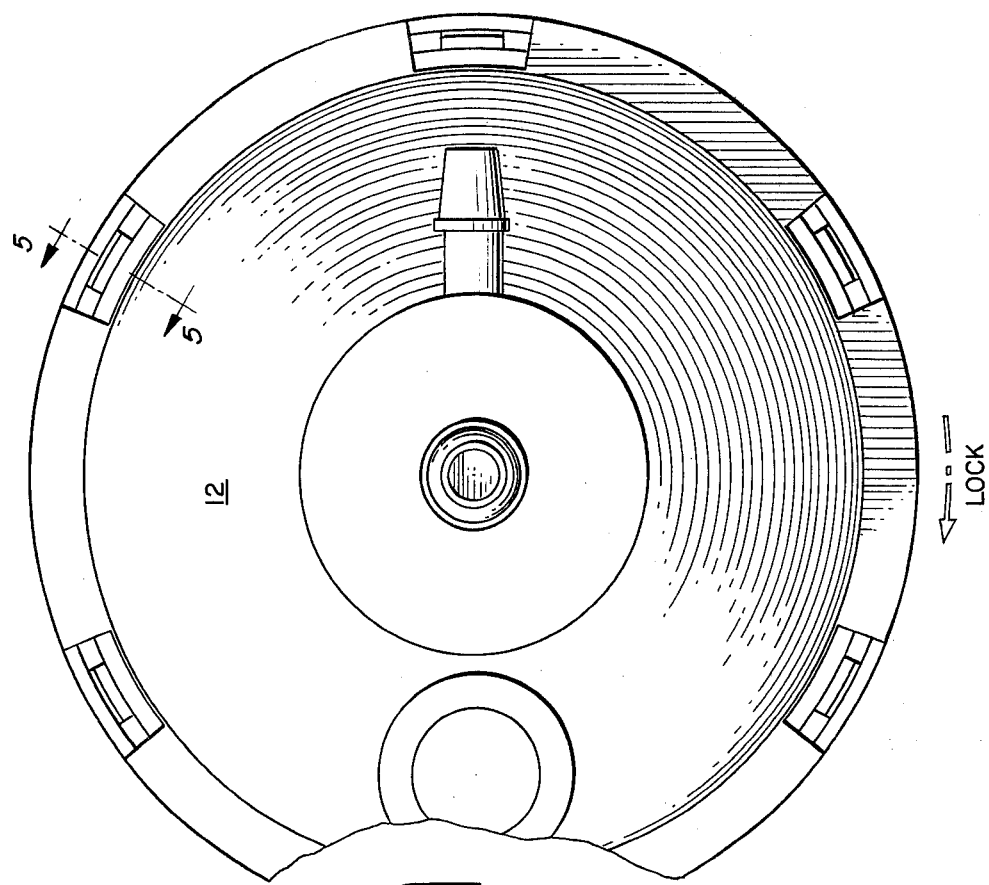
FIG. 2, is a top plan view of the container.
Figure 1:
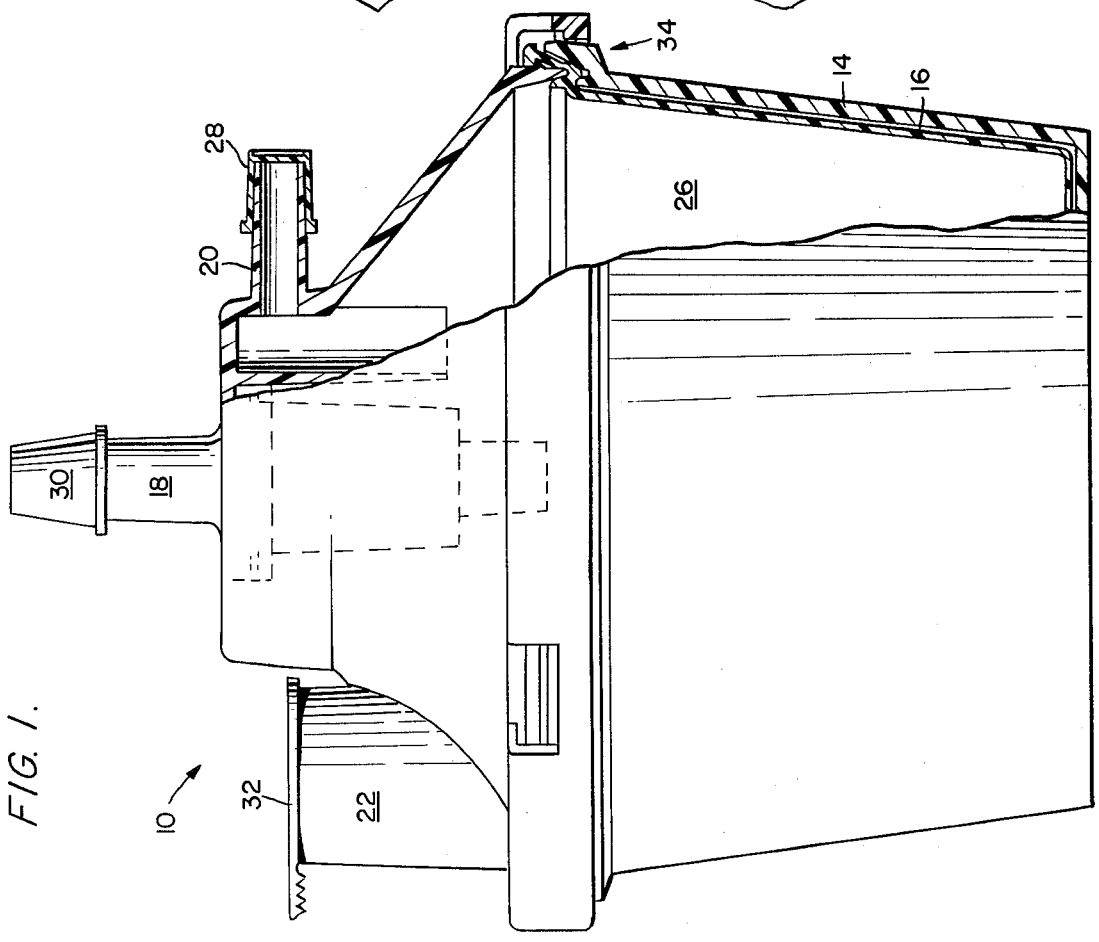
FIG. 1, is an elevation view of the medical suction container partially sectioned.

Referring to FIG. 1, there is illustrated a medical suction container 10 having a flat bottom for providing lateral stability on a flat horizontal surface. Container 10 comprises lid 12, canister 14 and flexible or molded plastic liner 16. Lid 12 which forms a closure portion for the open end of the canister comprises suction egress conduit port 18, patient ingress conduit port 20 and spout 22. Suction conduit port 18 and patient conduit port 20 extend through lid 12 and thereby communicate with interior volume 26 of medical suction container 10 as enclosed by liner 16 and lid 12. Both canister 14 and liner 16 are made of transparent plastic so that the level of entrained fluid can be visually monitored.

Suction conduit port 20 is often provided with a splash prevention means and a shutoff valve means to prevent fluids entrained in the liner of the container from entering and contaminating the suction source and vacuum lines.

As illustrated in FIG. 1, suction conduit port 18, patient conduit port 20 and spout 22 are closed by resealable caps 28, 30 and 32 respectively, to maintain the container in an aseptic condition. It is contemplated that the resealable caps in one embodiment, may be tethered to lid 12 by suitable tether means so that they will not be lost. More specifically, caps 28, 30 and 32 would be tethered to their respective conduits and spout.

When medical suction container 10 is to be used caps 28 and 30 are removed from suction conduit port 18 and patient conduit port 20. Suction conduit port 18 is connected to a vacuum source (not shown) and patient conduit port 20 is connected to a patient as desired. The vacuum source creates a vacuum within interior volume 26 which acts to draw fluid, such as puss, offal and other bodily matter from the patient through patient conduit port 20 and into interior volume 26 of container 10. After container 10 has been filled with bodily fluids suction conduit port 18 and patient conduit port 20 are resealed by caps 28 and 30. Cap 32 of spout 22 would then be removed so that the entrained fluids could be poured out. Alternatively, the conduit ports could be resealed and lid 12 and liner 16 could be disposed of together with the entrained fluids. This latter method of disposing of the fluids will be discussed in greater detail later in this disclosure.

Figure 3:
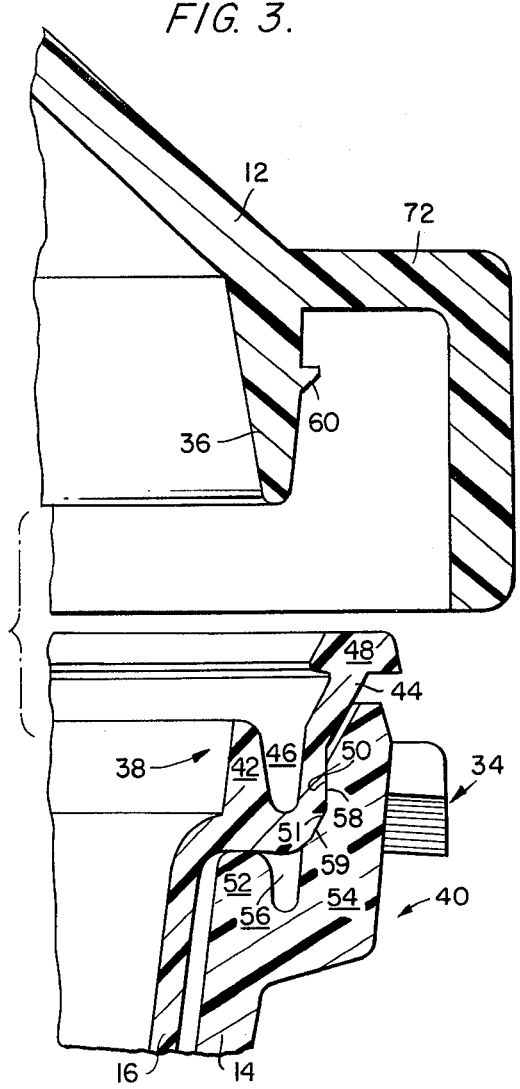
FIGS. 3 and 4, are fragmental cross-sectional views of the lid, the canister and the canister liner.
Figure 4:
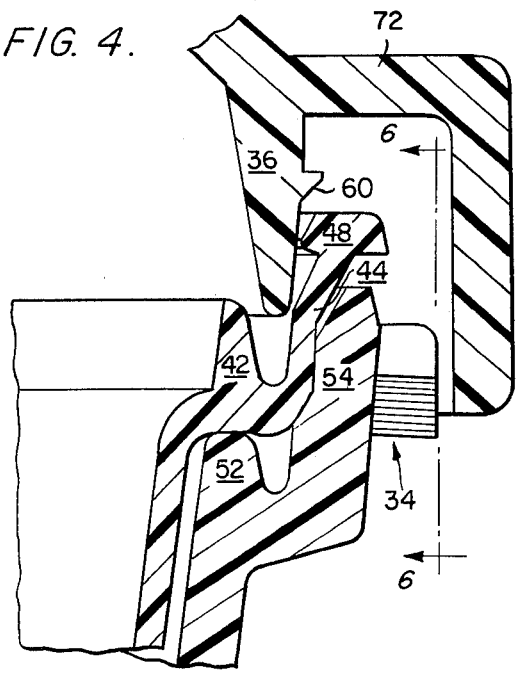
Figure 5:
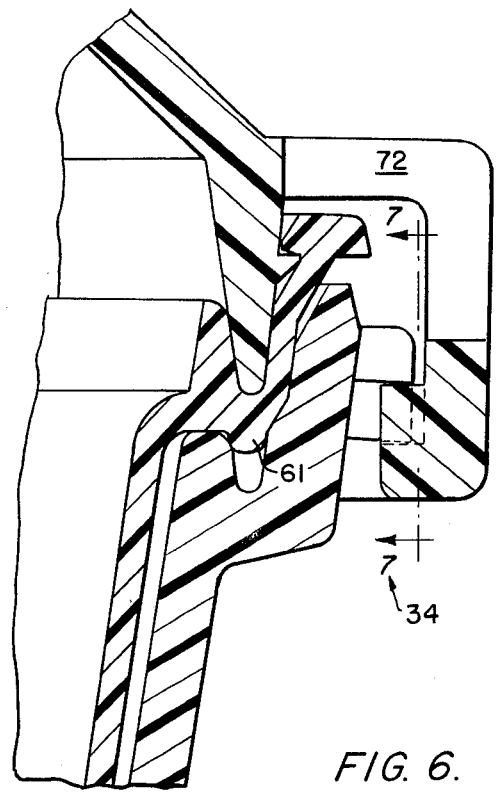
FIG. 5, is a fragmental cross-sectional view along line 5—5 of FIG. 1.

The principal feature of the present invention is the air tight seal maintained at sealing means 34. The details of sealing means 34, is best illustrated in FIGS. 3, 4 and 5. Sealing means 34 comprises sealing protrusion 36 of lid 12, liner sealing assembly 38 and canister sealing assembly 40. Sealing protrusion 36 is mated with liner sealing assembly 38 to form the air tight seal for interior volume 26.

Liner sealing assembly 38 comprises first upwardly extending liner portion 42 and second upwardly extending liner portion 44, between which annular liner notch 46 is formed. Second upwardly extending liner portion 44 further comprises locking lip 48 and opposed liner aligning surfaces 50 and 51.

Canister sealing assembly 40, forming an internal canister receiving means is similar to and located below liner sealing assembly 38. Canister sealing assembly 40 comprises first upwardly extending canister portion 52 and second upwardly extending canister portion 54 between which annular canister notch 56 is formed. Second upwardly extending canister portion 54 comprises canister aligning surfaces 58 and 59 which cooperate with opposed liner aligning surfaces 50 and 51 respectively. These opposed cooperating aligning surfaces position liner notch 46 directly over canister notch 56.

Sealing protrusion 36 of lid 12 forms a downwardly extending annular engaging member that further comprises lip 60. When sealing protrusion 36 is forced into mating position (illustrated in FIG. 5) with liner sealing assembly 38, locking lip 48 of liner sealing assembly 38, traps lip 60, thereby securing sealing protrusion 36 in the mating position. Forcing sealing protrusion 36 into liner notch 46 forces liner 16 and specifically base portion 61 of liner notch 46 into canister notch 56, which also forms an air tight seal between liner 16 and canister 14.

Figure 6:
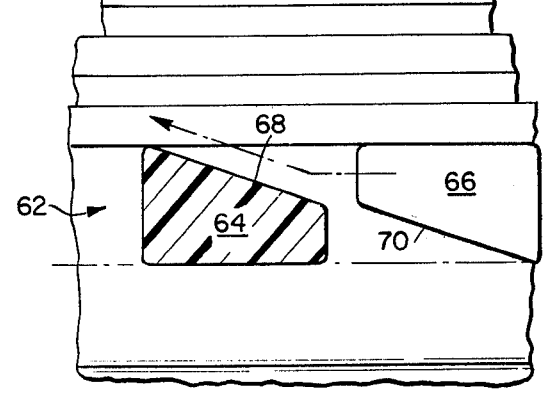
FIG. 6, is a fragmental cross-sectional view along line 6—6 of FIG. 4.
Figure 7:
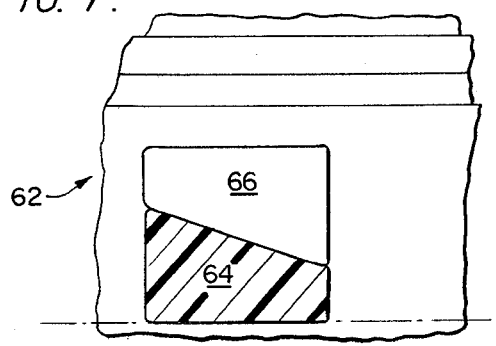
FIG. 7, is a fragmental cross-sectional view along line 7—7 of FIG. 5.
Figure 8:
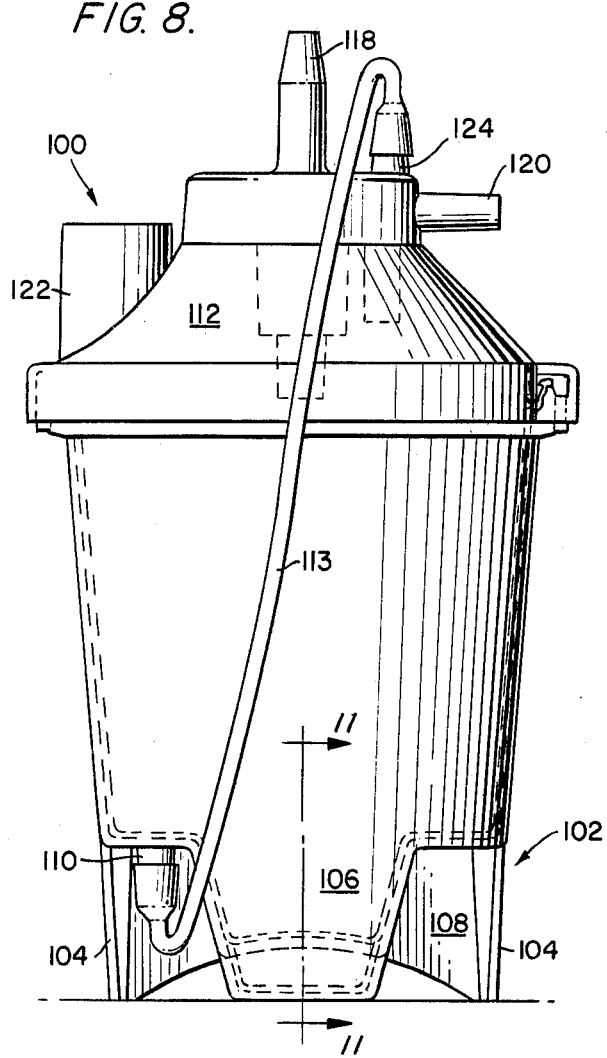
FIG. 8, is an elevation view of an alternate embodiment of the medical suction container.
Figure 9:
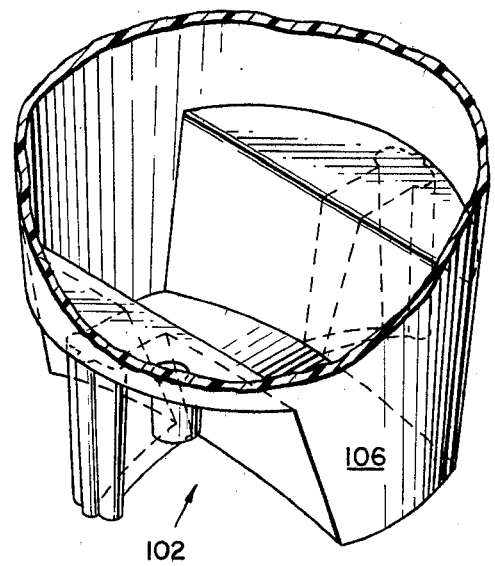
FIG. 9, is a fragmental perspective view of the container bottom of the alternate embodiment.
Figure 10:
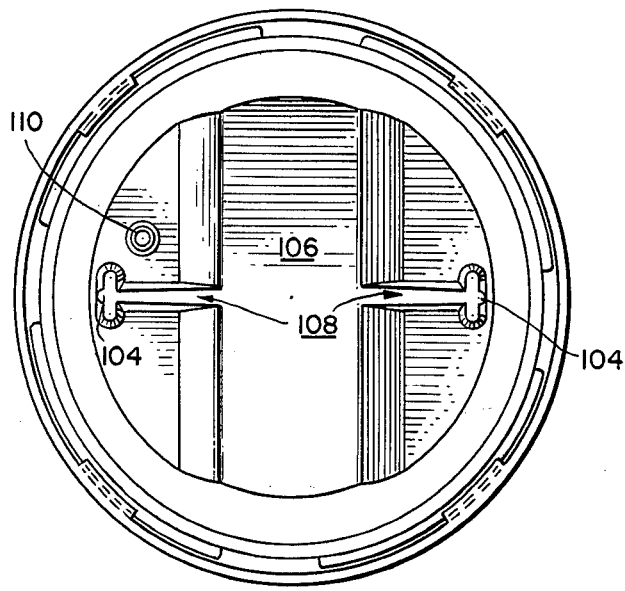
FIG. 10, is a bottom plan view of the alternate embodiment.
Figure 11:
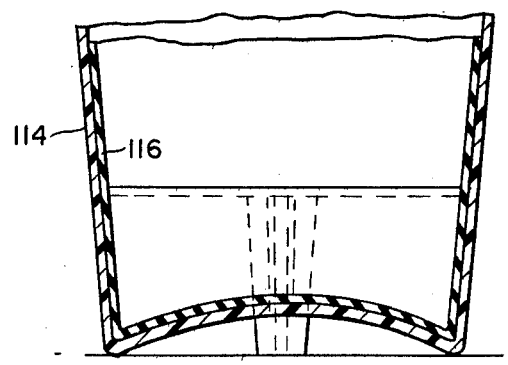
FIG. 11, is a fragmental cross-sectional view along line 11—11 of FIG. 8.

Sealing protrusion 36 is forced into a sealing or mating relationship with liner notch 46 by forcing means 62, best illustrated in FIGS. 6 and 7. Forcing means 62 comprises wedge-shaped lid camming blocks 64 and wedge-shaped canister camming blocks 66, disposed around the periphery of the canister and lid. Lid camming blocks 64 and canister camming blocks 66 have opposed engaging inclined camming surfaces 68 and 70, respectively. Rotating lid 12 in a clockwise direction, with respect to canister 14, engages forcing means 62, which slides inclined lid camming surface 68 along inclined canister camming surface thereby drawing lid 12 towards canister 14. Drawing lid 12 towards canister 14 forces sealing protrusion 36 into liner notch 46. Sealing protrusion 36 is then locked into this mating position by locking lip 48 which traps lip 60.

Lid camming blocks 64 are mounted on extended housing member 72. Housing member 72 covers and protects sealing means 34 from the surrounding environment.

FIGS. 8, 9, 10 and 11 illustrate an alternate embodiment comprising medical suction container 100. Base 102 of container 100 comprises two leg members 104 connected to bottom portion 106 by web members 108. Leg members 104 provide lateral stability to container 100 when it rests on a horizontal flat surface. The under surface of bottom portion 106 and web members 108 is dome-shaped and forms a concave bottom.

Lid 112 is provided with suction conduit port 118, patient conduit port 120 and spout 122 similar to the above described first embodiment. In addition, vent conduit port 124 is also provided and is connected by flexible hose 113 to vent 110, which is explained in greater detail below.

Of particular interest, with respect to the present invention is vent 110 which extends through base 102 and thereby communicates with the interior and exterior of canister 114. Vent 110 is provided so that trapped air can escape when liner 116 is inserted into canister 114. In addition, during the medical suction procedure vent 110 is connected to vent conduit port 124 in lid 112 by flexible hose 113 that serves to equalize pressure on both sides of liner 116. By equalizing the pressure the liner will not collapse during the medical suction procedure.

When either liner 16 of container 10 or liner 116 of container 100 is filled, the lids of the respective containers are rotated counterclockwise to disengage the opposed engaging camming surfaces. The lid with liner still locked thereto by the locking lip of the liner, can then be removed and discharged. A new liner and lid can then be utilized with the reusable container.

It has been determined that in surgical procedures where a high percentage of solid matter is entrained in the removed offal, it is desirable to use the subject container without the liner. Examples of such surgical procedures are orthopedic surgery where bone chips are entrained in the offal; and in dilation and curretage procedures where the scrappings of the uterus are entrained in the offal.

Both of the previously discussed and illustrated embodiments can be used without the liner in selected surgical procedures and would function similarly. When the medical suction container is used without the liner, sealing protrusion 36 mates directly with canister sealing assembly 40. As before the wedge-shaped camming blocks of forcing means 62 when rotated forces sealing protrusion 36 into a mating position with canister notch 56 forming an air tight seal therebetween.

Upon completion of the medical suction procedure, the appropriate ports are resealed by the resealing caps and the canister is disposed of together with the lid. The surgical setup of the medical suction container would be identical to a setup using a container with a liner.

The present invention provides for an air tight seal between a lid and a canister liner. So while the present invention has been disclosed in connection with the illustrated embodiments, it is not to be so limited but is to be limited solely by the claims which follow:

I claim:

1. A medical suction container comprising:
   a canister;
   a liner mounted within said canister having an open end and formed of a flexible material;
   a lid for said canister having a vacuum conduit port which is adapted to be attached to a suction line to create a vacuum within said liner, and a patient conduit port for receiving fluid from a patient during a medical suction procedure;
   a sealing means comprising a liner sealing assembly for providing a seal between said liner and said lid, and a canister sealing assembly for providing a seal between said canister and said liner;
   said liner sealing assembly comprises a sealing protrusion on said lid and a first upwardly extending liner portion and a second upwardly extending liner portion between which is formed a liner notch at the open end of said liner;
   said canister sealing assembly is disposed below said liner sealing assembly and comprises a first upwardly extending canister portion and a second upwardly extending canister portion between which is formed a canister notch; and
   a forcing means for forcing said sealing protrusion into said liner notch and extending said flexible material of said liner into said canister notch thereby forming a seal between said lid and said liner, and said liner and said canister.

2. A medical suction container according to claim 1 wherein said forcing means comprises a camming lid engaging surface on said lid and an opposed camming canister engaging surface on said canister which cooperate to force said sealing protrusion into said liner notch.

3. A medical suction container according to claim 2 wherein said sealing protrusion is provided with a locking lip and said lid is provided with a lip on said second upwardly extending liner portion, for engaging the locking lip to lock said liner to said lid.

4. A medical suction container according to claim 3 wherein said canister is provided with a vent which communicates with the interior of said canister and a vent conduit port on said lid by a flexible hose.

5. Container according to claim 4 wherein said canister of said medical suction container has a concave bottom.

6. Container according to claim 1 further comprising aligning means for aligning said liner notch with said canister notch, comprising aligning surfaces on said canister assembly and opposed aligning surfaces on said liner sealing assembly, said surfaces act to guide said liner into proper alignment so that said liner notch is aligned with said canister notch.

7. Container according to claim 6 wherein said aligning surfaces of said canister assembly are disposed on said second upwardly extending canister portion and said opposed aligning surfaces on said liner sealing assembly are disposed on said second upwardly extending liner portion.

8. Container according to claim 7 wherein said lid is rotated with respect to said canister to engage said opposed engaging camming surfaces of said forcing means thereby forcing said sealing protrusion into said liner notch.

9. Container according to claim 8 wherein said lid comprises an extended housing member for protecting said sealing assembly of said liner.

* * * * *